United States Patent [19]

Chatham

[11] 4,009,618
[45] Mar. 1, 1977

[54] REACTOR SAMPLER
[75] Inventor: Robert Michael Chatham, Cleethorpes, England
[73] Assignee: Continental Oil Company, Ponca City, Okla.
[22] Filed: Feb. 12, 1976
[21] Appl. No.: 657,671
[30] Foreign Application Priority Data
 Feb. 17, 1975  United Kingdom .............. 6592/75
[52] U.S. Cl. .............................................. 73/424
[51] Int. Cl.$^2$ ......................................... G01N 1/10
[58] Field of Search .......... 73/424, 422 TC, 421 A, 73/425.2, 425.4 R; 222/452

[56] References Cited
UNITED STATES PATENTS

| | | | |
|---|---|---|---|
| 2,973,645 | 3/1961 | Grimes et al. | 73/424 |
| 3,080,095 | 3/1963 | Woroble | 222/452 |
| 3,129,590 | 4/1964 | Ellis | 73/424 |
| 3,561,274 | 2/1971 | Haunschild | 73/424 |

Primary Examiner—S. Clement Swisher
Attorney, Agent, or Firm—Richard W. Collins

[57] ABSTRACT

Apparatus for removing a sample of particulate catalyst material from a reactor while the reactor is at operating conditions. The sampling apparatus includes an elongated tube terminating in a chamber located inside the reactor, the chamber having a valve at one end which opens to receive a catalyst sample and a valve at the other end which opens to deliver the catalyst sample to a sample receiver. A rotatable actuating shaft extending from outside the reactor to the sampling chamber enables an operator to selectively obtain a catalyst sample or deliver a previously obtained catalyst sample to a receiver. A stuffing box is attached to the end of the elongated tube outside the reactor and is removable therefrom. A turning member extending through the stuffing box engages the actuating shaft. The stuffing box may be detached and repacked without removing the rest of the sampling apparatus from the reactor.

10 Claims, 5 Drawing Figures

REACTOR SAMPLER

BACKGROUND OF THE INVENTION

1. Field of the Invention

This invention relates to apparatus for sampling the contents of reactor vessels and has particular reference to apparatus suitable for removing a sample of catalyst from a catalytic reforming reactor while the reactor is in the normal operating condition.

2. Description of the Prior Art

Sampling devices of the general type described herein are known, and usually comprise a sampling chamber or cavity located within a reactor, which chamber or cavity can be operated from outside the reactor to selectively obtain a catalyst sample and deliver same to a sample receiver while the reactor is at normal operating conditions.

A catalyst sampler of the general type to which this invention pertains is described in U.S. Pat. No. 3,129,590. Another variation of this type of catalyst sampler is described in U.S. Pat. No. 3,561,274. The samplers described therein include provision for manually operating a rotatable shaft to selectively obtain a catalyst from within the reactor and to deliver the sample to a receiver, all while the reactor is at operating conditions of high temperature and pressure. Samplers as described in the aforementioned patents, and particularly in U.S. Pat. No. 3,561,274, have proven quite satisfactory in many respects, and have been widely utilized in commercial refineries. The catalyst sampler according to the present invention is in many respects similar to the one described in U.S. Pat. No. 3,561,274, but has advantages and features not found in the prior art devices as will be pointed out in detail below. Samplers as described in U.S. Pat. No. 3,561,274 are subject to the disadvantage that it is necessary to remove the sampler from the reactor in order to change the seals therein. This is generally undesirable as such reactors, even when not operating, are generally maintained under a positive nitrogen pressure to protect the catalyst content and to keep air out of the reactor. There has accordingly been a need for a catalyst sampler which could enable a catalyst sample to be removed from an operating reactor, and which could also allow for packing material to be replaced without the necessity of opening the reactor to the atmosphere. Such a catalyst sampler is provided by the present invention.

SUMMARY OF THE INVENTION

According to the present invention a sampling apparatus for a reactor is provided which comprises an elongated tube or conduit extending into the interior of a reactor vessel. An end cap on the end of the elongated tube and a plate within the tube spaced from the end cap are provided. The cap and plate each have an opening therein and together with the conduit wall define a sample chamber or cavity within the reactor. An actuating rod extends substantially coaxial with the conduit. A pair of notched discs attached to the actuating rod provide first and second gate means for selectively obtaining a sample or delivering a sample from the chamber. The gate means are arranged so that with the first gate means in an open position the second gate means is in a closed position, and with the first gate means in a closed position the second gate means is in an open position.

A stuffing box is releasably secured to the elongated tube or conduit at the end thereof remote from the reactor, and a shaft within the stuffing box engages the actuating rod. One or more seal elements such as packing rings are provided within the stuffing box about the shaft and a packing gland and nut are provided for loading the seal elements to prevent substantial leakage of the reactor fluid therepast. Replacement of the seal elements in the stuffing box can be effected irrespective of the position of the first and second gate means. The replacement of the seals may be effected when the reactor is under a nitrogen blanket without opening the interior of the reactor to the atmosphere as one or the other of the gate means will be closed regardless of the valve actuating rod position.

The sampling conduit includes a sample delivery passage communicating therewith and disposed with its axis at an acute angle to the longitudinal axis of the elongated sampling conduit. The sample delivery passage may include one or more valves for isolating a sample collector chamber from the reactor.

It is an object of the present invention to provide a catalyst sampler for removal of a catalyst sample from a reactor operating at a high temperature and pressure without opening the reactor to the atmosphere.

It is a further object to provide such a catalyst sampler with provision for changing the seals thereof without removing the sampler from the reactor and without opening the reactor to the atmosphere.

The above as well as additional objects and advantages are provided by the present invention as will be apparent from a consideration of the following detailed description of the preferred embodiment thereof.

DESCRIPTION OF THE PREFERRED EMBODIMENT

Figure 1:
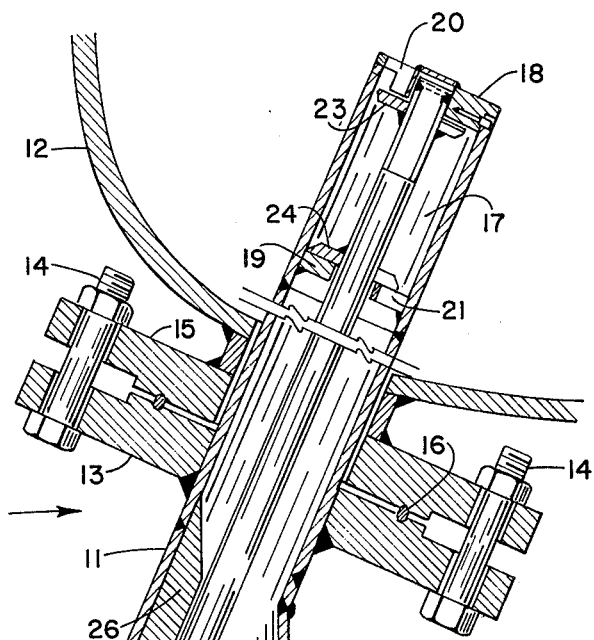
FIG. 1 is a view, partially in cross-section, showing the details of a sampler in accordance with the invention, and also showing its arrangement relative to a reactor vessel.
Figure 1:
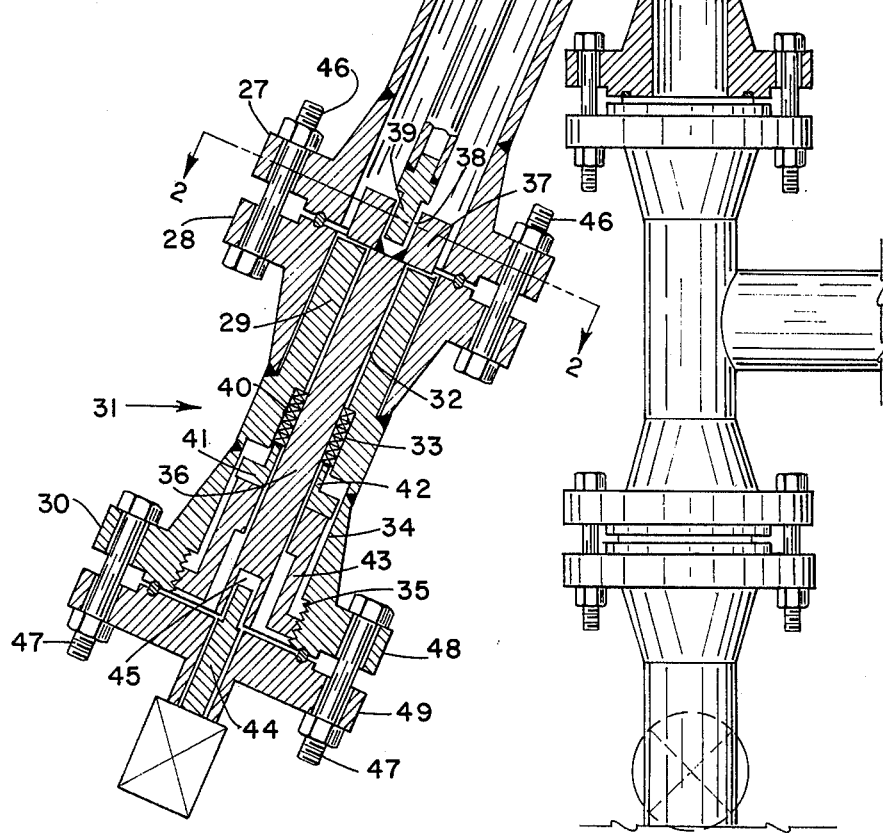

The most preferred embodiment of the invention will now be described by reference to the drawings. FIG. 1 best illustrates the overall device of the invention and its relationship to a reactor vessel containing a catalyst material to be sampled during operation of the reactor.

In FIG. 1, the sampling device of this invention is indicated generally at 10, and includes an elongated cylindrical tube 11 extending into the interior of a reactor 12. The sampling device 10 has a flange member 13 welded thereto and adapted to be connected by bolts 14 to matching flange member 15 attached to reactor 12. Sealing ring 16 between flange members 13 and 15 provides a fluid tight connection between the reactor interior and the upper exterior position of cylindrical tube 11.

Figure 3:
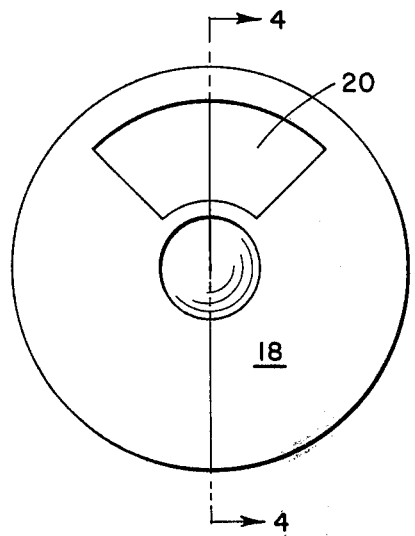
FIG. 3 is a top plan view of the end cap for the sampler.
Figure 4:
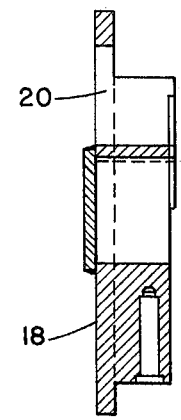
FIG. 4 is a cross-sectional view taken along the line 4—4 of FIG. 3.
Figure 5:
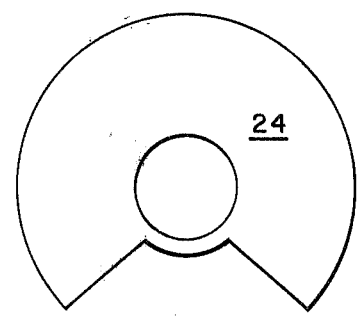
FIG. 5 is a plan view of a disc forming a part of a valve member of the sampler.

A sample chamber 17 is formed in the upper portion of tube 11 by the outer wall of tube 11, end cap 18, and plate 19 attached to the interior wall of tube 11. End cap 18, as seen more clearly in FIG. 3, includes an opening 20. A similar opening 21 is provided in plate 19. An elongated actuating rod 22 extends inside tube 11 to end cap 18, and rod 22 has a pair of notched discs 23 and 24 attached thereto and arranged so that either the opening 20 in end cap 18 or the opening 21 in plate 19 is closed at all times. Rotation of actuating rod 22 selectively opens and closes the respective openings.

A catalyst delivery tube 25 connects with tube 11 and provides a passageway from the bottom of sample chamber 17 to a sample receiving member (not shown).

The portion of the sampler downstream from delivery tube 25 is conventional, and does not constitute a part of the invention. As is known in the art, the sample receiving means generally includes valving and an inert gas system whereby the sample receiving means is purged with inert gas prior to receiving the catalyst sample so that the sampled catalyst is not subjected to an oxidizing atmosphere.

A former or diverter member 26 is located in tube 11 and serves to direct catalyst from chamber 17 to delivery tube 25.

The lower end of tube 11 has a flange member 27 which is connected to a matching flange member 28 which in turn is attached to sleeve 29. A lower flange member 30 is also attached to sleeve 29. Sleeve 29 and flange members 28 and 30 together constitute a stuffing box 31 having an internal passage 32, a counterbored passage 33, and an expanded bore 34. The lowermost section of expanded bore 34 has threads 35.

Figure 2:
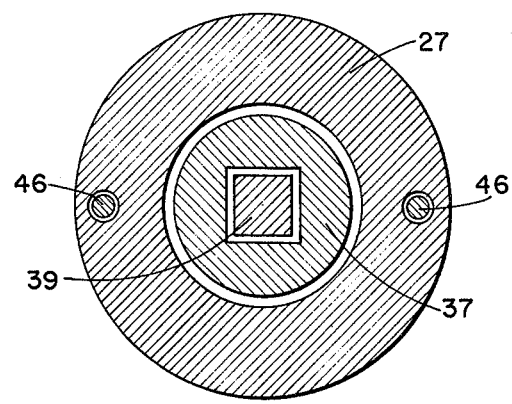
FIG. 2 is a cross-sectional view of a portion of the sampler taken along the line 2—2 of FIG. 1.

A turning member 36 extends through passage 32 and has an enlarged element 37 welded to its upper end above the end of sleeve 29. Enlarged element 37 has a shaped cavity 38 forming a socket into which shaped end member 39 on actuating rod 22 fits. The arrangement of enlarged element 37 and shaped end member 39 is also illustrated in FIG. 2. Rotation of turning member 36 causes rotation of enlarged element 37 which in turn causes rotation of actuating rod 22.

A series of packing rings 40 are located in counterbored passage 33 of sleeve 29 to provide a seal between the interior of tube 11 and the atmosphere. A packing gland 41 in expanded bore 34 includes an upper portion 42 shaped to fit into counterbored passage 33 and compress packing rings 40. A packing nut 43 in expanded bore 34 contacts the rear of packing gland 41, and is threadedly engaged with threads 35 such that rotation of packing nut 43 in the proper direction compresses packing rings 40 effecting the seal.

Rotation of turning member 36 is effected by rotation of stub shaft 44 which extends into a socket 45 formed in the lower end of turning member 36.

A particular advantage of the sampler described above over prior art samplers is that the sampler of this invention can be repacked with new packing rings 40 without removing the tube 11 from reactor 12. This feature provides important improvements in that removal of tube 11 from reactor 12 is undesirable even if the reactor is in a shutdown condition, as such reactors are normally pressurized with inert gas when not operating. The disadvantages of having to remove tube 11 from a pressurized reactor are apparent.

The procedure for repacking the sampler of this invention with new packing rings 40 without removing tube 11 from reactor 12 will now be described.

After the sampler 10 has been in use in reactor 12 for a period of time, such as 2 or 3 years, at which point the packing rings 40 are subject to deterioration and failure, and preferably while the reactor is in a shutdown condition, actuating rod 22 is positioned so that disc 24 covers the opening in plate 19. Bolts 46 joining flange members 27 and 28 are then removed, and the flange members 27 and 28 are separated. Bolts 47 are then removed, permitting separation of flange member 48 attached to the lower end of stuffing box 31 and flange member 49 carrying stub shaft 44. Turning member 36 is then removed from sleeve 29, packing nut 43 is removed from expanded bore 34 of stuffing box 31, and packing gland 41 is also removed from expanded bore 34. Packing rings 40 are then removed from counterbored passage 33 in sleeve 29, and new packing rings are inserted. The dismantling procedure is then reversed, and the stuffing box 31 is re-assembled and rejoined to elongated cylindrical tube 11. It is apparent from the above discussion that the sampler according to this invention can be repacked without removing the sampler from the reactor to which it is attached.

The normal operation of the sampler of this invention is straightforward, and will now be briefly described. Actuating rod 22 is normally positioned such that disc 23 closes the opening 20 in end cap 18, and when it is desired to remove a sample of catalyst from reactor 12, actuating rod 22 is rotated until the notch in disc 23 matches the opening 20 in end cap 18 so that catalyst particles from the reactor 12 can enter sample chamber 17. With the actuating rod in this position, disc 24 on actuating rod 22 is positioned to close the opening 21 in plate 19 attached to tube 11 so that catalyst particles entering sample chamber 17 are retained therein. Rotation of actuating rod 22 to its original position results in disc 23 closing the opening in end cap 18, and also results in the opening of disc 24 matching the opening in plate 19 such that catalyst particles from sample chamber 17 fall by gravity down tube 11 and subsequently into delivery tube 25. As mentioned previously, known procedures for evacuating and purging the sample receiver (not shown) are utilized such that the catalyst sample does not come in contact with an oxidizing atmosphere during the sampling procedure.

The foregoing description of the preferred embodiment of a sampler in accordance with the invention is exemplary and numerous modifications and variations will be apparent to those skilled in the art. However, it is an essential feature of this invention that the packing means in the sampler be replaceable without the necessity of removing the sampler from the reactor to which it is attached.

What is claimed is:

1. A sampling apparatus for removing a sample of particulate solid catalyst from the interior of a reactor comprising:
   a. an elongated tube member having an end cap with an opening therein;
   b. an actuating rod extending through said tube member and having a pair of discs attached thereto, each of said pair of discs having a notched opening therethrough, and said pair of discs being spaced longitudinally one from the other;
   c. a plate member in said elongated tube member longitudinally spaced from said end cap, said plate member being affixed to the interior of said tube member and having a first opening therethrough through which said actuating rod extends, said plate member having a second opening therethrough for delivery of catalyst particles;

d. a sample chamber defined by the portion of said elongated tube member between said end cap and said plate member, said sample chamber being selectively open to or isolated from the interior of a reactor in which it is located, and said sample chamber being selectively open to or isolated from a sample delivery means attached to said sampler;

e. a turning member engageable with said actuating rod for rotation of said actuating rod, said turning member extending through a stuffing box detachably affixed to said elongated tube member, said stuffing box comprising a sleeve having a bore therethrough, said bore including a counterbored section and an expanded bore section terminating in a threaded section;

f. packing ring means in the counterbored section of said bore and about the turning member extending therethrough;

g. a packing nut in the expanded bore portion of the stuffing box threadedly engaged with the expanded bore section of said stuffing box; and h. a packing gland between said packing nut and said packing ring means.

2. A sampling apparatus as defined in claim 1 wherein said turning member includes at one end an enlarged element having a shaped opening therein for engagement with the end of said actuating rod.

3. A sampling apparatus as defined in claim 2 wherein said turning member includes at its other end a socket for engagement with a means for turning said turning member.

4. A sampling apparatus as defined in claim 3 including a stub shaft carried by said stuffing box and engageable with said turning member for rotation thereof.

5. A sampling apparatus for removal of a sample of particulate catalyst material from a reactor comprising:

a. an elongated tube member having an actuating member extending therethrough and having a sample chamber at one end thereof selectively open to or closed from the interior of a reactor and correspondingly closed from or open to a passage means extending from said sample chamber to a sample delivery means;

b. a stuffing box detachably affixed to the other end of said elongated member;

c. turning means extending through said stuffing box for engagement with and rotation of said actuating member, said turning means being removable from said stuffing box when said stuffing box is detached from said elongated tube member; and d. adjustable packing means in said stuffing box.

6. A sampling apparatus according to claim 5 wherein said stuffing box includes an adjustable packing nut.

7. A sampling apparatus according to claim 6 wherein said stuffing box includes a sleeve with a bore therethrough, said bore including a first section at one end thereof, a second central section larger in diameter than said first section, and a third section at the other end thereof larger in diameter than said second section.

8. A sampling apparatus according to claim 7 wherein said elongated tube member and said stuffing box are joined together by matching flange members having a sealing ring therebetween.

9. A sampling apparatus according to claim 8 wherein said turning means includes socket means at one end thereof for engagement with said actuating member, said socket means having an outer diameter greater than the diameter of said first section of the bore through said sleeve.

10. A sampling apparatus according to claim 9 wherein said sample delivery means comprises a delivery tube extending from said elongated tube member and terminating in a flange member for connection with a sample receiving means.

* * * * *